United States Patent [19]
Thompson et al.

[11] Patent Number: 4,731,326
[45] Date of Patent: Mar. 15, 1988

[54] DISEASE DIAGNOSIS BY DETECTION OF SHED NORMAL TISSUE ANTIGENS

[75] Inventors: Russell E. Thompson, Marshfield; Robert H. Rubin; Nina T. Rubin, both of Brookline; Teresa H. Chan, Burlington, all of Mass.

[73] Assignee: Ortho Diagnostic Systems Inc., Raritan, N.J.

[21] Appl. No.: 616,991

[22] Filed: Jun. 4, 1984

[51] Int. Cl.$^4$ ............... G01N 33/535; G01N 33/545; G01N 33/574; G01N 33/577
[52] U.S. Cl. ..................................... 435/7; 435/172.2; 435/240.27; 436/520; 436/526; 436/531; 436/534; 436/548; 436/804; 436/813
[58] Field of Search ............... 436/548, 520, 526, 531, 436/534, 804, 813; 435/7, 240, 172.2

[56] References Cited
U.S. PATENT DOCUMENTS

| | | | |
|---|---|---|---|
| 4,376,110 | 3/1983 | David | 436/548 X |
| 4,447,545 | 5/1984 | DeFazio et al. | 436/518 |
| 4,471,058 | 9/1984 | Smith | 436/548 X |
| 4,474,892 | 10/1984 | Murad | 436/548 X |
| 4,650,756 | 3/1987 | Old | 435/68 |

OTHER PUBLICATIONS

H. J. Sachse et al., "Development of a Radioimmunoassay for a High Molecular Mass Tubular Antigen in Urine–Its Application for Early Detection of Tubular Damage", Clinica Chimica Acta, 110:91–104 (1981).
J. M. Wellwood et al., "Urinary N-Acetyl-$\beta$-D--Glucosaminidase Assays in Renal Transplant Recipients", Transplantation, pp. 396–400, (1978).
A. W. Mondorf et al., "Brush Border Enzymes and Drug Nephrotoxicity" Acute Renal Failure, Marcel Dekker, New York (1983).
D. Pierard et al., "Monoclonal Antibodies as Tools for Kidney Damage Diagnosis", Clinical Assays, vol. 31:1047–1050 (1983).
W. P. Schrader et al., "Immunoassay of the Adenosine Deaminase Complexing Proteins of Human Tissue and Body Fluids", The Journal of Biological Chemistry, vol. 254, 23:11958–63 (1979).
K. Jung et al., "Influence on pH on the Activity of Enzymes in Urine at 37° C.", Chem. 25,965 (1980) Abstract.
M. D. Bastable, "$\beta_2$-Microglobulin in Urine: Not Suitable for Assessing Renal Tubular Function", Clinical Chemistry, vol. 29, 5:996–997 (1983).
R. Ueda et al., Proc. Nat'l Acad. Sci. U.S.A., 78, 5122–5126 (1981).

*Primary Examiner*—Sidney Marantz
*Attorney, Agent, or Firm*—Mark A. Hofer

[57] ABSTRACT

Methods are provided for the detection of proximal convoluted tubule causing diseases or kidney harmful drug monitoring by detecting the presence of shed normal proximal tubule associated antigens in a body fluid such as urine. The preferred embodiment employs an ELISA sandwich format wherein one monoclonal antibody specific for a first epitopic site on said antigen is immobilized on a solid phase and a second antibody, specific for a second epitopic site on said antigen is directly or indirectly labeled.

55 Claims, No Drawings

4,731,326

DISEASE DIAGNOSIS BY DETECTION OF SHED NORMAL TISSUE ANTIGENS

FIELD OF THE INVENTION

This invention relates to immunoassays in general, and in particular, provides means for diagnosing renal specific diseases and for monitoring renal affecting drugs by detecting the presence of shed, normal renal tissue antigens.

BACKGROUND OF THE INVENTION

The detection of specified antigens (defined as a substance whose introduction into an animal stimulates the production of antibodies capable of reacting specifically therewith), haptens (a substance requiring additional accessory materials before its introduction into an animal stimulates the production of antibodies specific therefor), analytes and the like substances (hereinafter collectively referred to as antigens) in body fluids such as blood, sputum, urine, and the like has in recent years become of utmost importance in both the research and clinical environments. The detection of antigens, and antibodies can often be related to various disease states and consequently is of extreme usefulness in diagnosis as well as gaining basic understandings concerning the genesis of disease as well as monitoring the effectiveness and side effects of therapies therefor.

One organ for which immunoassays for disease conditions is constantly sought, is the kidney. Early efforts in this regard have typically focused on detecting various renal associated enzymes. For instance, Wellwood et al. described such a method in an article entitled "Urinary N-Acetyl-$\beta$-D-Glucosaminidase Assay In Renal Transplant Recipients" (Transplantation 26: 396–400, 1978) wherein urinary NAG activity was measured in an attempt to assess renal related cellular injury. In particular, it was hoped that NAG would prove to be a valuable aid in the early diagnosis of renal transplant rejections. Unfortunately, other causes including oliguria, hypotension, chronic rejection, renal vein thrombosis, and gentamicin administration also resulted in altered NAG excretion levels thus greatly reducing the utility of any NAG related assay due to its non-specificity.

Similar studies by Mondorf et al. ("Brush Border Enzymes and Drug Nephrotoxicity", Acute Renal Failure, Editor Solez and Whelton, Marcel Dekker, Inc., ISBN 0-8247-1904-2, 1984) attempted to correlate drug induced renal cell damage with excreted brush border enzymes such as alanine aminopeptidase (AAP) and the presence of cellular fragments. The assays were typically performed utilizing isotopically labeled, gel filtration purified high molecular weight kidney antigens. These studies, like those of Wellwood et al., obtained results which were difficult to correlate with specific renal diseases, in particular diseases or conditions affecting particular internal kidney structures. Jung et al. ("Influence of pH on the Activity of Enzymes in Urine at 37° C.", Clinical Chemistry Vol. 28, 8: 1814, 1982), and Bastable ($\beta_2$-Microglobulin in Urine: Not Suitable for Assessing Renal Tubular Function", Clinical Chemistry Vol. 29, 5: 996–997, 1983) have indicated that questionable results may be due in large measure to the variable effects associated with urine pHs. The less than physiological pHs typical of urine deleteriously affects enzyme activity, often in a nonrepeatable manner.

Sachse et al. have described ("Development of a Radioimmunoassay for a High Molecular Mass Tubular Antigen in Urine-Its Application for Early Detection of Tubular Damage", Clinica Chimica Acta. 110: 91–104, 1981) the detection of enzymes and uncharacterized antigenic components of undisclosed high molecular mass and their relation to kidney cellular damage through inhibition binding experiments with isotopically labeled urinary antigens. A practical assay specific for particular renal cell type damage, however, was not disclosed; such being still another object of the present invention.

It is an object of the present invention to provide an assay suitable for the detection of specific renal associated diseases.

It is a related object of the present invention to provide assays capable of detecting proximal tubule damaging diseases.

It is yet another object of the present invention to provide a means for detecting renal associated diseases by assaying for shed normal, renal tissue associated antigens in body fluids.

It is yet another related object of the present invention to avoid reliance upon conventional renal enzyme detection schemes.

It is yet a further related object to provide means for monitoring drugs and particularly levels thereof which may be capable of inducing renal cellular damage.

Ueda et al., at Sloan-Kettering Cancer Center, described the isolation and reactivity of seventeen monoclonal antibodies derived from fusions with spleen cells of mice immunized with established culture lines of renal cancers ("Cell Surface Antigens of Human Renal Cancer Defined by Mouse Monoclonal Antibodies: Identification of Tissue-specific Kidney Glycoproteins", Proc. Natl. Acad. Sci., Vol. 78: 5122–5126, 1981). That work resulted in the description of nine cell surface antigenic systems including the most restricted antigens gp160, $S_{25}$, and gp120r. The primary object of those studies was to identify cancer specific antigens, however, none of the mouse antibodies cited in that publication were successful in that regard.

It is a further related object of the present invention to build upon the work of Ueda et al. by identifying which of the Ueda antibodies may be used in the manner of the present invention to derive an assay meeting the desired and stated object.

SUMMARY OF THE INVENTION

In acordance with the objects and principles of the present invention, there are described new assays suitable for detecting diseases which involve the proximal convulated tubules of the kidneys. It has been discovered that such diseases including acute pyelonephritis and acute tubular necrosis may be detected and/or diagnosed by determining the presence of shed normal antigens in a body fluid such as urine. Further, the instant assay is useful for monitoring drugs which are known to cause deleterious renal related side effects such as, for example, the cephalosporins and aminoglycosides.

In particular, the instant assay methods employ certain of the monoclonal antibodies (or their preferred, later developed equivalents) described by the Ueda et al. group, supra, capable of specifically detecting the 120,000 molecular weight glycoprotein (gp120r) in a format suitable for practical implementation in the clinical laboratory. Although the assays may be formatted in a variety of ways, the most preferred embodiment utilizes an ELISA sandwich approach wherein a first monoclonal antibody, specific for one epitopic site on the glycoprotein antigen, is immobilized and a second monoclonal antibody, specific for a second epitopic site on the same antigen, serves to couple a detectable entity to the thusly immobilized antigen. Accordingly, in the most preferred embodiment, the detectable entity is an enzyme whose presence is determined by the development of a detectable product from a supplied substrate.

Alternative assay embodiments comprise different detection schemes based on the type of detection entity employed as well as the method of detection and include both heterogeneous and homogeneous formats.

Further, the assays of the present invention are suitable for monitoring proximal tubule damage caused by those classes of drugs known to result in renal damage including, for example, the cephalosporins and aminoglycosides.

DETAILED DESCRIPTION OF THE INVENTION AND BEST MODE

It will be readily appreciated by those skilled in the art that a variety of mechanisms may be employed for detecting the occurrence of an immunological reaction. Typically these techniques revolve around labeling one or the other components of an antigen (the term antigen is used herein to inclusively describe antigens, haptens, ligands, synthetic peptides, anti-idiotype antibodies and the like) or antibody (the term antibody is used herein to inclusively describe binding partners specific to antigens, antibodies, antibody fragments such as F(ab) and F(ab)$'_2$ and the like) and then detecting the association of that label with the immunological complex resulting from the specific reaction of the two components. A variety of formats have evolved over the years including heterogeneous (one or the other unreacted components are removed) or homogeneous (the immunological reaction is detected in the presence of unreacted components) based on a variety of combinations of competitive, noncompetitive, reverse, forward, and simultaneous type formats. It is not the purpose of this disclosure to go into detail regarding these various well-known formats, suffice it to say that various investigators have found it useful to employ them with a variety of detectable entities including fluorescent molecules, chemiluminescent molecules, light absorbing dyes, light scattering molecules, gold particles, red blood cells, micro and macroparticles of both natural and man-made origin, magnetic particles, isotopes, and enzymes. Except for enzymes, virtually all of the other detectable entity or labels may be detected directly utilizing appropriately designed instrumentation, also readily available. With enzymes, an additional step is generally required, that of presenting a suitable substrate upon which the enzyme acts to produce a product which is in turn detected in much the same manner as the foregoing labels. Further, the detectable entities may comprise the label itself (direct labeling) or may merely be a binding partner specifically reactive with the label or another binding partner associated with the label which is added subsequently to the immunological reaction (indirect labeling).

As has been previously intimated, the instant invention may be utilized in a variety of generally accepted immunoassay formats, however, based on simplicity and sensitivity, a sandwich type format such as that described by David et al. in U.S. Pat. No. 4,376,110 is preferred.

In such a format, suitable for the detection of an antigen possessing multiple epitopes, one antibody specific for a first epitope is immobilized upon a solid phase while a second "labeled" antibody reacts with a second epitopic site on the antigen thereby forming a "sandwich" type complex which may be readily detected. The solid phase may be provided in a variety of forms and includes, for instance, the walls of a microtiter tray well, an accessory paddle type device, microbead or particles, and the like. Procedures for adsorbing or covalently attaching antibodies to such surfaces are also generally well-known. Similarly, the detectable entity on the second antibody may be any of the well-known labels attached directly or indirectly to the antibody by methods readily available to the investigator.

The instant invention is additionally versatile in that it may be employed in homogeneous formats utilizing repetitive pattern recognition type instruments and methods such as is described in copending application of L. A. Kamentsky entitled "Immunoassay Methods Employing Patterns for the Detection of Soluble and Cell Surface Antigens", U.S. Ser. No. 455,765, U.S. Pat. No. 4,487,839. The Kamentsky invention relies upon detection of areas alternating with the presence or absence (or alternatively, immunological deactivation) of the immunological component (antigen and antibody) in order to derive a signal which is integrated positively and negatively, respectively, over time for providing information concerning the immunological component to be detected. Alternatively, a conventional heterogeneous format may be utilized wherein the solid phase, containing the "sandwich" if antigen is present, is substantially removed from unreacted components and the detectable entity associated with either the soluble or solid phase is detected and related to the presence of antigen in the sample. Such removal steps may be accomplished by a variety of means such as washing, spraying or other mechanical expedients also well-known.

The present invention may also be used with another class of homogeneous formats employing the so-called donor-acceptor type of fluorescent labels. Such labels have been described, for instance, by Ullman et al. in U.S. Pat. Nos. 4,199,559; 3,996,345; 4,174,384; and 4,261,968. In such instances, both the first and second antibodies specific to different epitopic sites on the antigen, are each labeled with one of a fluorescerquencher pair of molecules wherein the fluorescer molecules are excited by light of a specified wavelength and fluoresce at a longer wavelength. The presence of a quencher molecule in close proximity to the fluorescer, however, results in quenching of this fluorescence thereby contributing to a decrease in measurable fluorescence. Thus, with increasing concentrations of antigen, more opportunities are provided for the attachment of antibodies, more fluorescence is quenched and a lower level of fluorescence exhibited.

Still alternatively, either one of the antibodies of the present invention may be used separately in order to detect the presence of the antigen. Such a modality is especially useful with competitive type assays wherein the antigen present in the body fluid sample is made to compete with a reagent supplied antigen or anti-idiotype antibody for the binding site on the antibody. Appropriate labeling of the reagent supplied antigen or anti-idiotype antibody and the detection of that label associated with the antibody specific for the antigen, permits determination of the concentrations of original antigen in the body fluid sample.

Still other alternative detection methods may be employed with the instant invention including the use of flow cytometry instruments. The principles of flow cytometry generally include hydrodynamic focusing wherein cells, particles or antigens, are encased in a sheath fluid and forced to flow, substantially in a single file fashion, through a focused illumination zone. Based upon light scattering and fluorescent properties exhibited upon passage through the focused illumination zone, identification may be accomplished. An example of such a flow cytometry instrument useful with the present invention is the SPECTRUM III ™, commercially available from the assignee hereof. With such an instrument, the entire assay is conducted in the soluble phase, detection of antigens being accomplished by detecting the immunological reaction of the antigen with either one or both of the antibodies of the instant invention, described later, which antibodies would typically be associated with a detectable entity having light scatter or fluorescent type characteristics suitable for detection by such an instrument.

The instant invention provides for new application of the $S_{23}$ and $S_{27}$ antibodies discovered by the Ueda et al. group at Memorial Sloan-Kettering Cancer Center. (It will be noted parenthetically that the Ueda et al. article cited earlier describes an $S_6$ antibody which has subsequently been replaced with an antibody, $S_{27}$, having substantially the same reactivity as the $S_6$ antibody but with preferable binding characteristics and is accordingly preferred herein.) The $S_{23}$ and $S_{27}$ antibody are the result of hybridoma cell lines deposited in the American Type Culture Collection as ATCC No. HB8540 and ATCC No. HB8428, respectively.

These antibodies and their equivalents may also be characterized by their reactivity with a number of cell lines available from either the ATCC or Memorial Sloan-Kettering Cancer Center as set forth in Table 1.

In short, the $S_{23}$ antibody is an $IgG_1$ isotype formed from immunizing cell line SK-RC-7 (renal cancer) having observed frozen tissue section reactivity with the epithelial cells of proximal tubules in the human kidney. The $S_{27}$ antibody is similar to the $S_{23}$ but is also seen to react with some frozen tissue portions of the loop of Henle in the human kidney. Reactivities were determined with immunofluorescence staining techniques and direct microscopic observation. Both antibodies identify a 120,000 mw glycoprotein and demonstrate minimal cross-reactivities with other human tissue. The $S_{23}$ and $S_{27}$ antibodies are individually commercially available in unconjugated form from the assignee hereof under the trademarks ORTHO URO-4a and ORTHO URO-4.

TABLE 1

| Cells[2] | Ab $S_{23}$ | | Ab' $S_6$[1] | |
|---|---|---|---|---|
| | Titer × $10^{-3}$ | Abs. | Titer × $10^{-3}$ | Abs. |
| Epithelial cancers: | | | | |
| Renal | | | | |
| SK-RC-1 (AA) | 1 | + | 50 | + |
| SK-RC-2 (AB) | — | — | 50 | + |
| SK-RC-4 (AE) | 50 | + | 50 | + |
| SK-RC-6 (AG) | 10 | + | 1000 | + |
| SK-RC-7 (AX) | 1 | + | 500 | + |
| SK-RC-8 (BE) | 1 | + | 50 | + |
| SK-RC-9 (BM) | — | + | 500 | + |
| SK-RC-11 (BZ) | 1 | + | 1000 | + |
| SK-RC-21 (EB) | — | — | 500 | + |
| SK-RC-28 (EU) | 500 | + | 5000 | + |
| SK-RC-29 (BW) | — | — | 50 | + |
| A-498 | — | + | 50 | + |
| CaKi-1 | — | — | 50 | + |
| Bladder | | | | |
| RT-4 | — | — | — | — |
| 5637 | — | — | — | — |
| T-24 | — | — | 5 | + |
| 253J | — | — | 5 | + |
| Breast | | | | |
| AlAb | — | — | — | — |
| BT-20 | — | — | — | — |
| MCF-7 | — | — | — | — |
| SK-BR-3 | — | — | — | — |
| Cervix | | | | |
| ME-180 | — | — | — | — |
| Colon | | | | |
| HT-29 | — | — | 5 | + |
| SW-1222 | — | — | — | — |
| Lung | | | | |
| SK-LC-LL | — | — | — | — |
| SK-LC-6 | — | — | 50 | + |
| Ovary | | | | |
| SK-OV-3 | — | — | — | — |
| Testicular | | | | |
| SK-GR-1 | — | — | — | — |
| Astrocytomas: | | | | |
| AJ, AS, BE | — | — | 5 | + |
| Melanomas: | | | | |
| SK-MEL-13,28,29,37,41 | — | — | — | — |
| SK-MEL-19 | — | — | — | — |
| Neuroblastomas: | | | | |
| SK-NMC, SK-NSH | — | — | — | — |
| Lymphoblastoid cells: | | | | |
| EBV B cells | | | | |
| AX, BE, EU | | | — | |
| Burkitt's lymphomas | | | | |
| Raji, Daudi | — | | — | |
| T cells | | | | |
| MOLT-4, T-45 | — | | — | |
| Normal human cells: | | | | |
| Kidney epithelium | | | | |
| ID | 10 | + | 5 | + |
| EQ, HY | 1.5 | + | 5 | + |
| GM, FR | 3 | + | 5 | + |
| EI, IJ | 1.5 | + | 5 | + |
| EG, GR, IB | 0.5 | + | 5 | + |
| Fetal kidney | | | | |
| C-4, C-3 | — | — | >5 | + |
| C-6 | — | — | >5 | + |

[1] Subsequent to this publication, Ueda et al. discovered an alternative antibody, $S_{27}$, having substantially the same reactivity as $S_6$ but having preferable binding characteristics and accordingly $S_6$ has been replaced with $S_{27}$ both in their studies and herein.

[2] Generally available from either ATCC, Memorial Sloan-Kettering Cancer Center, or a number of other academic institutions.

EXAMPLE 1

I. Immunization and Antibody Production

Generation of murine monoclonal antibodies have been described by Ueda et al., supra in detail. Briefly, (BALB/c × C57BL/6)Fl mice were immunized with established renal cancer cell lines. Spleen cells were harvested and fused with MOPC-21 NS/1 myeloma cells in the presence of polyethylene glycol. Hybridoma cultures were cloned by limiting dilution until stable lines were obtained. Antibodies were characterized against a panel of cell lines and against tissue specimens as set forth in Table 1. Ascites was produced by injecting the hybridoma lines subcutaneously into nu/nu mice of Swiss background.

II. Monoclonal Antibody Purification $S_{23}$ and $S_{27}$ were purified from ascitic protein using a Protein A affinity column pursuant to the methods of Ey et al. (Immunochemistry 15: 429-36, 1978) and Seppala et al. (Scand. J. Immunol. 14: 335-42, 1981). Antibodies were eluted from the column with a 0.01M citrate buffer, pH 4.5. Alternatively, antibodies can be purified on a DEAE Affi-Gel blue column using the procedure of Bruck et al. (J. of Immunol. Methods 53: 313-19, 1982). Antibody activity was monitored against the renal cell line, SR-RC-7, by a two-step immunofluorescent procedure, using a fluorescein labeled goat anti-mouse IgG. Evaluation of fluorescent intensity was made using the ORTHO Spectrum III ™ flow cytometer.

III. Antibody Conjugation $S_{23}$ was conjugated with horseradish peroxidase (HRP) according to the method of Wilson and Nakane (In Immunofluorescence and Related Staining Techniques, ed W. Knapp et al. p215, 1978). Free HRP was removed by ammonium sulfate fractionation. Optimal signal to noise ratios were determined by titering the $S_{23}$-HRP conjugate versus nonspecific mouse IgG and $S_{27}$ coated microtiter plates in the assay described below.

IV. Solid Phase Configuration

Protein A purified $S_{27}$ was passively adsorbed onto the surfaces of Immunlon 2 microtiter plates (Dynatech Corporation). 125 ul of $S_{27}$ at a concentration of 10 ug/ml in 0.01M $NA_2CO_3/NaHCO_3$ buffer was allowed to adsorb overnight at 4° C. The plates were then washed with a phosphate buffered saline solution containing 0.05% Tween 20 (PBST). Any remaining binding sites were blocked with 1% bovine serum albumin in phosphate buffered saline (PBS). The plates were washed again with PBST prior to use.

V. Standard Urine Preparation

Standards were prepared from a pool of patient urines with optical density values exceeding 2.0 in the assay described below. The standard was aliquoted and stored at $-70°$ C. until used in the assay. Assay standards and controls were prepared from the standard urine by dilution in 0.1% bovine serum albumin in PBS.

VI. Assay Protocol 100 ul of patient urine, assay controls, and known assay standards was added to previously prepared $S_{27}$ coated microtiter plates. Urines were incubated for one hour at 25° C. Nonbound antigen was aspirated out and the plates were washed three times with PBST. $S_{23}$-HRP was added and incubated for one hour at 25° C. Nonbound conjugated antibody was aspirated away and the plate was washed three times with PBST prior to the addition of the enzyme substrate ortho-phenylenediamine. Color development was permitted for one hour at 25° C. whereupon enzymatic action was halted with the addition of 4.5M sulfuric acid. Patient values were determined by comparison to known values. Enzymatic activity was quantitated by measuring color development at 490 nm. A linear standard curve was generated and arbitrary units of reactivity (A.U.) were assigned.

Within assay precision was 5.2-7.2% and between assay precision was 6-12.2%. Normal urine specimens were assayed and had a mean of 0.05 O.D. units. Patients with acute tubular necrosis, drug or dye induced toxicity in kidney transplants demonstrated elevated levels of antigen ranging from 0.5 to more than 10 O.D. units. Patients with glomerular disease, hereditary nephritis and polycystic disease were also assayed and some reactivity observed.

Results are summarized in the Figure. Utilizing a cut off of $\approx 0.5$ O.D., specificity of the instant assay for tubular disease is readily apparent. It should be noted that those patients suffering from acute tubular necrosis were largely suffering as a result of treatment with aminoglycosides. Accordingly, correlation between drug induced renal damage and the presence of shed antigens from normal tissue as detected by $S_{23}$ and $S_{27}$ is very high.

EXAMPLE 2

Assay Protocol For Simultaneous Assay

To $S_{27}$ coated microtiter plates, prepared pursuant to the methods of Example 1, 100 ul of patient urine, assay controls, and known assay standards is added. Conjugated $S_{23}$-HRP is added simultaneously with the samples to be assayed and the mixture incubated for one hour at 25° C. Thereafter, the solid phase is washed three times with PBST. The enzyme substrate ortho-phenylenediamine is added for one hour at 25° C. for color development, detected as set forth in Example 1.

All references cited herein are to be deemed fully incorporated herein by reference.

It will be readily apparent to those skilled in the art that numerous alternatives to the foregoing example methods or labels and as indicated in the specification may be possible without departing from the spirit or scope of the present invention.

What is claimed is:

1. A method for diagnosing disease or other conditions affecting the proximal tubules of the human kidney resulting in the release of normal proximal tubule associated antigens into a body fluid comprising the steps of:
   (a) providing a solid phase surface having immobilized thereon a first antibody produced by cell line deposited as ATCC HB8540 or ATCC HB8428 and specific for a first epitopic site on said antigen;
   (b) providing a second antibody from the other of said deposited cell lines, said second antibody having associated therewith a detectable entity and specific for a second epitopic site on said antigen;
   (c) contacting said first and second antibodies with said body fluid sample suspected of containing the proximal tubule associated antigen to be detected under conditions suitable for immunological reactions whereby said antigen reacts with said first and second antibodies to form a sandwich complex;
   (d) detecting the entity associated with said sandwich complex whereby the presence of said antigen may be determined.

2. The method as provided in claim 1 wherein the step of contacting said antigen with said second antibody for promoting an immunological reaction therebetween to form a first immunological complex is performed prior to contacting said first immunological complex with said first antibody under conditions for promoting an immunological reaction therebetween to form said sandwich complex.

3. The method as provided in claim 1 wherein the step of contacting said antigen with said first antibody for promoting an immunological reaction therebetween to form a second immunological complex is performed prior to contacting said second immunological complex with said second antibody under conditions for promoting an immunological reaction therebetween to form said sandwich complex.

4. The method as provided in claim 2 further comprising the step of substantially removing said body fluid sample and second antibody which has not reacted and, said detecting step comprises detecting the entity associated with said body fluid sample or with said solid phase following said removing step.

5. The method as provided in claim 3 further comprising the step of substantially removing said body fluid sample and second antibody which has not reacted and, said detecting step comprises detecting the entity associated with said body fluid sample or with said solid phase following said removing step.

6. The method as provided in claim 2 wherein said detecting step further comprises reacting said detectable entity with a binding partner conjugate specifically reactive with said entity, said binding partner conjugate comprising a detectable label.

7. The method as provided in claim 3 wherein said detecting step further comprises reacting said detectable entity with a binding partner conjugate specifically reactive with said entity, said binding partner conjugate comprising a detectable label.

8. The method as provided in claim 1 wherein said detecting step is selected from the group consisting of detecting fluorescence, detecting chemiluminescence, detecting phosphorescence, detecting isotopes, detecting magnetic particles, detecting light absorbance, detecting light scatter, detecting enzymes, detecting red blood cells, detecting microspheres, and detecting macroparticles.

9. The method as provided in claim 2 wherein said detecting step is selected from the group consisting of detecting fluorescence, detecting chemiluminescence, detecting phosphorescence, detecting isotopes, detecting magnetic particles, detecting light absorbance, detecting light scatter, detecting enzymes, detecting red blood cells, detecting microspheres, and detecting macroparticles.

10. The method as provided in claim 3 wherein said detecting step is selected from the group consisting of detecting fluorescence, detecting chemiluminescence, detecting phosphorescence, detecting isotopes, detecting magnetic particles, detecting light absorbance, detecting light scatter, detecting enzymes, detecting red blood cells, detecting microspheres, and detecting macroparticles.

11. The method as provided in claim 4 wherein said detecting step is selected from the group consisting of detecting fluorescence, detecting chemiluminescence, detecting phosphorescence, detecting isotopes, detecting magnetic particles, detecting light absorbance, detecting light scatter, detecting enzymes, detecting red blood cells, detecting microspheres, and detecting macroparticles.

12. The method as provided in claim 5 wherein said detecting step is selected from the group consisting of detecting fluorescence, detecting chemiluminescence, detecting phosphorescence, detecting isotopes, detecting magnetic particles, detecting light absorbance, detecting light scatter, detecting enzymes, detecting red blood cells, detecting microspheres, and detecting macroparticles.

13. The method as provided in claim 6 wherein said detecting step is selected from the group consisting of detecting fluorescence, detecting chemiluminescence, detecting phosphorescence, detecting isotopes, detecting magnetic particles, detecting light absorbance, detecting light scatter, detecting enzymes, detecting red blood cells, detecting microspheres, and detecting macroparticles.

14. The method as provided in claim 7 wherein said detecting step is selected from the group consisting of detecting fluorescence, detecting chemiluminescence, detecting phosphorescence, detecting isotopes, detecting magnetic particles, detecting light absorbance, detecting light scatter, detecting enzymes, detecting red blood cells, detecting microspheres, and detecting macroparticles.

15. The method as provided in claim 1 wherein said detecting step comprises providing a substrate for said entity when said entity comprises an enzyme and detecting the presence of product produced as a result of enzymatic activity on said substrate.

16. The method as provided in claim 2 wherein said detecting step comprises providing a substrate for said entity when said entity comprises an enzyme and detecting the presence of product produced as a result of enzymatic activity on said substrate.

17. The method as provided in claim 3 wherein said detecting step comprises providing a substrate for said entity when said entity comprises an enzyme and detecting the presence of product produced as a result of enzymatic activity on said substrate.

18. The method as provided in claim 4 wherein said detecting step comprises providing a substrate for said entity when said entity comprises an enzyme and detecting the presence of product produced as a result of enzymatic activity on said substrate.

19. The method as provided in claim 1 wherein said providing solid phase step comprises providing a solid phase having said first antibody immobilized thereon in a specific pattern of areas alternating with the presence and absence of said antibody.

20. The method as provided in claim 2 wherein said providing solid phase step comprises providing a solid phase having said first antibody immobilized thereon in a specific pattern of areas alternating with the presence and absence of said antibody.

21. The method as provided in claim 3 wherein said providing solid phase step comprises providing a solid phase having said first antibody immobilized thereon in a specific pattern of areas alternating with the presence and absence of said antibody.

22. The method as provided in claim 1 further comprising the step of comparing the detected entity against a plurality of standard having known concentrations of antigen for determining the concentration of said human kidney associated antigens in said body fluid sample.

23. The method as provided in claim 2 further comprising the step of comparing the detected entity against a plurality of standard having known concentrations of antigen for determining the concentration of said human kidney associated antigens in said body fluid sample.

24. The method as provided in claim 3 further comprising the step of comparing the detected entity against a plurality of standard having known concentrations of antigen for determining the concentration of said human kidney associated antigens in said body fluid sample.

25. The method as provided in claim 13 further comprising the step of comparing the detected entity against a plurality of standard having known concentrations of antigen for determining the concentration of said human kidney associated antigens in said body fluid sample.

26. The method as provided in claim 14 further comprising the step of comparing the detected entity against a plurality of standard having known concentrations of antigen for determining the concentration of said human kidney associated antigens in said body fluid sample.

27. A method for detecting conditions resulting in the shedding of normal human kidney associated antigens into a body fluid comprising the steps of:
(a) providing a first antibody produced by the cell lines deposited in ATCC HB8540 or ATCC HB8428 and specific for a first epitopic site on said antigen, said first antibody having associated therewith either the acceptor or donor molecules of a fluorescent energy transfer pair;
(b) providing a second antibody from the other of said ATCC cell lines, said second antibody having associated therewith the other of said acceptor-donor molecules and specific for a second epitopic site on said antigen;
(c) contacting said first and second antibodies with said body fluid sample suspected of containing the antigens to be detected under conditions suitable for immunological reactions whereby said antigen reacts with said first and second antibodies;
(d) illuminating said acceptor and donor molecules at a frequency selected to substantially excite said donor molecules but not said acceptor molecules; and
(e) detecting light emitted by said acceptor molecules or said donor molecules and relating same to the presence or absence of said antigen to be detected.

28. The method as provided in claim 1 wherein said first and second antibodies have reactivities substantially as set forth in Table 1.

29. The method as provided in claim 2 wherein said first and second antibodies have reactivities substantially as set forth in Table 1.

30. The method as provided in claim 3 wherein said first and second antibodies have reactivities substantially as set forth in Table 1.

31. The method as provided in claim 6 wherein said first and second antibodies have reactivities substantially as set forth in Table 1.

32. The method as provided in claim 13 wherein said first and second antibodies have reactivities substantially as set forth in Table 1.

33. The method as provided in claim 14 wherein said first and second antibodies have reactivities substantially as set forth in Table 1.

34. The method as provided in claim 27 wherein said first and second antibodies have reactivities substantially as set forth in Table 1.

35. A method for drug monitoring comprising performing the method of claim 1 and relating increasing levels of antigen presence to increasing drug levels whereby renal damage may be assessed.

36. A method for drug monitoring comprising performing the method of claim 2 and relating increasing levels of antigen presence to increasing drug levels whereby renal damage may be assessed.

37. A method for drug monitoring comprising performing the method of claim 3 and relating increasing levels of antigen presence to increasing drug levels whereby renal damage may be assessed.

38. A method for drug monitoring comprising performing the method of claim 6 and relating increasing levels of antigen presence to increasing drug levels whereby renal damage may be assessed.

39. A method for drug monitoring comprising performing the method of claim 7 and relating increasing levels of antigen presence to increasing drug levels whereby renal damage may be assessed.

40. A method for drug monitoring comprising performing the method of claim 13 and relating increasing levels of antigen presence to increasing drug levels whereby renal damage may be assessed.

41. A method for drug monitoring comprising performing the method of claim 14 and relating increasing levels of antigen presence to increasing drug levels whereby renal damage may be assessed.

42. A method for drug monitoring comprising performing the method of claim 27 and relating increasing levels of antigen presence to increasing drug levels whereby renal damage may be assessed.

43. A method for drug monitoring comprising performing the method of claim 28 and relating increasing levels of antigen presence to increasing drug levels whereby renal damage may be assessed.

44. A method for detecting the presence of normal proximal convoluted tubule tissue associated antigen in urine comprising the steps of reacting said urine with either one or both antibodies produced by cell lines ATCC HB8540 or ATCC HB8428 and detecting label associated with said reacted antibodies.

45. The method as provided in claim 44 wherein said detecting step is accomplished by detecting light scatter and/or light fluorescence by the principles of flow cytometry whereby an immunological reaction between said antigen and said labeled antibody or antibodies is detected whereby the presence of said antigen in said urine may be determined.

46. The method as provided in claim 44 further comprising before said detecting step, the step of removing unreacted antibodies and said detecting step comprises detecting label associated with said reacted antibodies or with said unreacted antibodies.

47. The method as provided in claim 44 wherein said detecting step is selected from the group consisting of detecting fluorescence, detecting chemiluminescence, detecting phosphorescence, detecting isotopes, detecting magnetic particles, detecting light absorbance, detecting light scatter, detecting enzymes, detecting red blood cells, detecting microspheres, and detecting macroparticles.

48. A method for detecting the presence of normal human kidney associated antigens in urine comprising competitively reacting said antigen with an antibody produced by cell line ATCC HB8540 specific for said sample antigen and reagent antigen having substantially similar reactivity with said antibody as said sample antigen, said reagent antigen having associated therewith a detectable label; and detecting label associated with said antigen which has reacted with said antibody or with said antigen which has not reacted with said antibody for determining the presence of said antigen in said sample.

49. The method as provided in claim 48 further comprising before the detecting step, the step of removing unreacted sample antigens and reagent antigens and said detecting step comprises detecting label associated with said reacted antigens or with said unreacted antigens.

50. The method as provided in claim 49 wherein said antibody is immobilized on a solid substrate.

51. The method as provided in claim 50 wherein said detecting step is selected from the group consisting of detecting fluorescence, detecting chemiluminescence, detecting phosphorescence, detecting isotopes, detecting magnetic particles, detecting light absorbance, detecting light scatter, detecting enzymes, detecting red blood cells, detecting microspheres, and detecting macroparticles.

52. A method for detecting the presence of normal human kidney associated antigens in urine comprising competitively reacting said antigen with an antibody produced by cell line ATCC HB8428 specific for said sample antigen and reagent antigen having substantially similar reactivity with said antibody as said sample antigen, said reagent antigen having associated therewith a detectable label; and detecting label associated with said antigen which has reacted with said antibody or with said antigen which has not reacted with said antibody for determining the presence of said antigen in said sample.

53. The method as provided in claim 52 further comprising before the detecting step, the step of removing unreacted sample antigens and reagent antigens and said detecting step comprises detecting label associated with said reacted antigens or with said unreacted antigens.

54. The method as provided in claim 53 wherein said antibody is immobilized on a solid substrate.

55. The method as provided in claim 54 wherein said detecting step is selected from the group consisting of detecting fluorescence, detecting chemiluminescence, detecting phosphorescence, detecting isotopes, detecting magnetic particles, detecting light absorbance, detecting light scatter, detecting enzymes, detecting red blood cells, detecting microspheres, and detecting macroparticles.

* * * * *

UNITED STATES PATENT AND TRADEMARK OFFICE
CERTIFICATE OF CORRECTION

PATENT NO. : 4,731,326

DATED : March 15, 1988

INVENTOR(S) : Russell E. Thompson et al

It is certified that error appears in the above-identified patent and that said Letters Patent is hereby corrected as shown below:

Claim 44, column 12, line 36: "antigen" should read -- antigens --.

Signed and Sealed this

Eleventh Day of July, 1989

Attest:

DONALD J. QUIGG

Attesting Officer

Commissioner of Patents and Trademarks